US007248672B2

(12) United States Patent
Durst et al.

(10) Patent No.: US 7,248,672 B2
(45) Date of Patent: Jul. 24, 2007

(54) MULTIPLE-POSITION X-RAY TUBE FOR DIFFRACTOMETER

(75) Inventors: Roger D. Durst, Middleton, WI (US); Bob Baoping He, Madison, WI (US)

(73) Assignee: Bruker AXS, Inc., Madison, WI (US)

( * ) Notice: Subject to any disclaimer, the term of this patent is extended or adjusted under 35 U.S.C. 154(b) by 0 days.

(21) Appl. No.: 11/111,497

(22) Filed: Apr. 21, 2005

(65) Prior Publication Data

US 2006/0239408 A1 Oct. 26, 2006

(51) Int. Cl.
*H01J 35/00* (2006.01)
*H05G 1/02* (2006.01)

(52) U.S. Cl. ............... 378/121; 378/119; 378/193; 378/197

(58) Field of Classification Search ............ 378/119, 378/121, 124, 134, 136–138, 140, 143, 148, 378/161, 193, 196–198
See application file for complete search history.

(56) References Cited

U.S. PATENT DOCUMENTS

| 3,336,494 A | * | 8/1967 | Nagashima et al. | ......... 378/121 |
| 4,234,794 A | * | 11/1980 | Voinea et al. | ................. 378/12 |
| 4,866,749 A | * | 9/1989 | Uematu | ....................... 378/134 |
| 4,870,671 A | * | 9/1989 | Hershyn | ....................... 378/124 |
| 4,899,354 A | * | 2/1990 | Reinhold | ....................... 378/34 |
| 5,515,414 A | * | 5/1996 | d'Achard Van Enschut et al. | ...... 378/141 |
| 5,822,395 A | * | 10/1998 | Schardt et al. | ............... 378/137 |
| 6,122,344 A | * | 9/2000 | Beevor | ........................ 378/88 |
| 6,151,381 A | * | 11/2000 | Grodzins et al. | ............. 378/90 |
| 6,266,392 B1 | * | 7/2001 | Fujinawa et al. | ........... 378/149 |
| 6,333,967 B1 | | 12/2001 | Osaka et al. | |
| 6,754,302 B2 | * | 6/2004 | Kitaoka | ....................... 378/34 |
| 7,110,503 B1 | * | 9/2006 | Kumakhov | .................. 378/119 |

FOREIGN PATENT DOCUMENTS

| DE | 38 27 511 A1 | 3/1989 |
| JP | 01-204337 | 8/1989 |
| JP | 05-314937 | 11/1993 |
| JP | 07-065759 | 3/1995 |

\* cited by examiner

*Primary Examiner*—Allen C. Ho
(74) *Attorney, Agent, or Firm*—Law Offices of Paul E. Kudirka

(57) ABSTRACT

An x-ray source provides both a line focus output and a point focus output, and is mounted on a rotatable support to allow easy changing between the two. A housing has ports at different angular positions relative to an anode, and each port has an associated optic appropriate for an x-ray beam passing through that port. Three or four ports may also be used to allow for different types of beam conditioning. The different beam optics may also do conditioning based on wavelength, and the anode may be of a composite material to provide different wavelength ranges. The rotatable support may be manual or motorized, and a lockout mechanism may be used to ensure that only one port is active at a time. The support may also be located on a movable table that is movable in multiple perpendicular directions.

23 Claims, 3 Drawing Sheets

MULTIPLE-POSITION X-RAY TUBE FOR DIFFRACTOMETER

FIELD OF THE INVENTION

This invention relates generally to the field of x-ray diffraction and, more particularly, to x-ray sources used in x-ray diffraction systems.

BACKGROUND OF THE INVENTION

Modern x-ray diffraction experiments use x-ray tubes that are optimized to deliver a line focus or a point focus onto the sample. The optimal type of focus depends on the details of the experiment being performed. For example, for experiments involving standard powder samples, a line focus is the preferred geometry while, for two dimensional diffraction or single crystal diffraction measurements, a point focus is preferred. However, as many users may have the need to conduct experiments on different types of samples, it may be desirable to switch between point and line focus as the situation warrants. Conventionally, this is accomplished by exchanging the optics mounted on the x-ray tube. For example, a single mirror used to redirect the x-ray beam produces a line focus, and this mirror can be exchanged with a pair of focusing mirrors (e.g., a so-called "Kirkpatrick-Baez" mirror pair), which will create a point focus.

Although functional, the changing of x-ray optics presents several drawbacks. Firstly, the optics must be exchanged manually, (and must typically be realigned after the exchange), which is inconvenient, labor-intensive and time consuming. Secondly, when a point focus optic is installed on the line focus port of an x-ray tube, it tends to focus only the x-rays from a small fraction of the tube onto the sample. As such, the x-ray flux achieved is smaller than that which could be achieved by using a point focus port. The point focus port is a port that is located at 90 degrees relative to the line focus port, and is oriented at a shallow, oblique angle relative to the electron beam focus, and which thereby projects the electron line focus on the anode into an apparent x-ray spot.

In U.S. Pat. No. 5,515,414 an x-ray tube is provided with flexible cooling water connections that allow the position of the x-ray tube to changed by 90 degrees to switch between point focus and line focus modes. However, to make the change, the tube must be removed from the tube shield, rotated manually, and reinserted into the shield. The optics used with either configuration appears to be the same, unlike the prior art systems described above.

U.S. Pat. No. 4,866,749 describes an x-ray tube with two cathodes: one that, when energized, produces a point focus; and the other that produces a line focus. When in the different modes, the optics used appear to remain the same. In addition, only the electron focus on the anode is changed and not the inclination of the anode, so that the point focus has a relatively low intensity.

SUMMARY OF THE INVENTION

In accordance with the present invention, an x-ray source is provided that includes an anode with an active area from which x-rays are emitted. The active area may be oblong such that an x-ray beam in a first direction has a substantially linear cross section while, in a second direction, a beam is generated that has a substantially spot-shaped cross section. A housing surrounds the anode, and has a plurality of ports through which x-rays can exit the housing. These ports are located along the perimeter of the housing at different angular positions relative to the anode. Thus, depending on the particular relative position of a port, the x-ray beam reaching it might be a line focus type beam or a point focus type beam.

The housing of the x-ray source is attached to a rotatable support that allows the housing to be rotated to different angular positions relative to the anode. Thus, in a first angular position, the housing is oriented so a first one of the ports is facing a given direction, such as the direction of a sample. In a second angular position, however, a second one of the housing ports is oriented so that it faces the given direction. In this way, x-ray beams with different shapes can be selected to face the first direction, e.g., so that the selected beam encounters the sample.

Attached to the housing adjacent to each port is a conditioning optic. Each optic includes optical components specifically intended for conditioning the type of beam that exits the housing through its adjacent port. Thus, for a port that receives an x-ray beam with a linear cross section, the associated optic would have line focus conditioning components. Likewise, for a port that receives an x-ray beam with a spot-shaped cross section, the associated optic would have point focusing conditioning optics. Typically, line focusing optics (and ports) would be positioned at a 90° angle from point focusing optics (and ports), relative to the position of the anode.

The housing has a plurality of ports, with either two, three or four being the most common. The use of three or four ports provides the option of having multiple optics conditioning the same beam shape with different optical components. This may be of use, for example, if different parts of the wavelength spectrum output by the anode are processed by different optics. The anode may also be of a composite material, such that it generates x-rays having multiple spectra. In such a case, different optics may be selected to process x-ray energy in the different wavelength spectra.

The mounting of the housing on a rotatable support provides for a simple way for a user to change between different x-ray beam characteristics, including different beam shapes and different wavelength characteristics. The support is attached to a fixed portion, and it rotates relative to the fixed portion as well as relative to the sample. The fixed portion may also be mounted on a movable surface that allows movement in different perpendicular directions, such as a vertical direction and a horizontal direction relative to the position of the sample. A lockout mechanism may be included with the x-ray system that is in communication with a shuttering system used for opening the various ports of the housing. As one example, an electrical switch may be established between the fixed portion and the rotatable support. Multiple switch contacts on the rotatable support, each associated with a different one of the ports, would align with a contact on the fixed portion at different angular positions of the housing. Switch contact would be required to allow gating of the ports and, in this way, only one of the ports could be used at a time.

BRIEF DESCRIPTION OF THE DRAWINGS

The above and further advantages of the invention may be better understood by referring to the following description in conjunction with the accompanying drawings in which.

DETAILED DESCRIPTION

Figure 1:
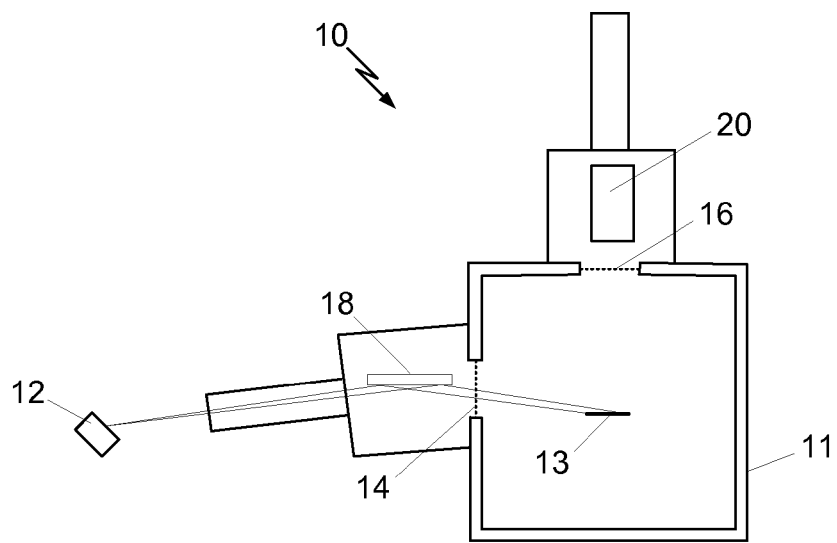
FIG. 1 is a cross-sectional schematic view of an x-ray source according to the invention oriented in a first angular position.

Shown schematically in FIG. 1 is a top view of an x-ray source 10 according to the present invention. The x-ray source has a housing 11 and resides adjacent to a sample 12 onto which x-ray energy is to be focused. The housing contains a conventional x-ray tube and has two ports 14, 16, via which x-ray energy may be output to the sample 12. Although all of the details of the x-ray tube are not shown in FIG. 1, the position of the target anode 13 is indicated. As in conventional systems, the anode is shaped like a line with a small finite width, and radiates in different directions, resulting in different x-ray beam cross-sections depending on the direction. Thus, for the configuration of FIG. 1, from the direction of port 14, the beam has the appearance of a spot while, from the direction of port 16, the shape of the beam is linear.

With the apparatus oriented as shown in FIG. 1, the port 16 and line focus optics are inactive. However, the port 14 and point focus optics 18 are positioned to direct x-ray energy to the sample 12. As shown, the x-ray energy that reaches the port 14 has a spot shape and, when gated through the port 14, may be properly handled by the point focus optics to create the desired point focus on the sample.

The point focus optic 18 differs from the line focus optic 20 in that it contains optical components specifically desired for the point focus application. Such optical components are known, and may include cross-coupled mirrors or a crystal monochromator with a pinhole aperture, or possibly another combination of monochromator, mirrors or filters. The line focus optic includes known optical components as well, ones that are specifically suited for the desired line focus application. These may include a single mirror or crystal, or other arrangement of components such as mirrors, monochromator or filter. Each of the optics may be pre-mounted and prealigned, and may be attached to the housing of the x-ray tube 10. As shown in the figure, the optics are mounted at 90° relative to each other.

Figure 2:
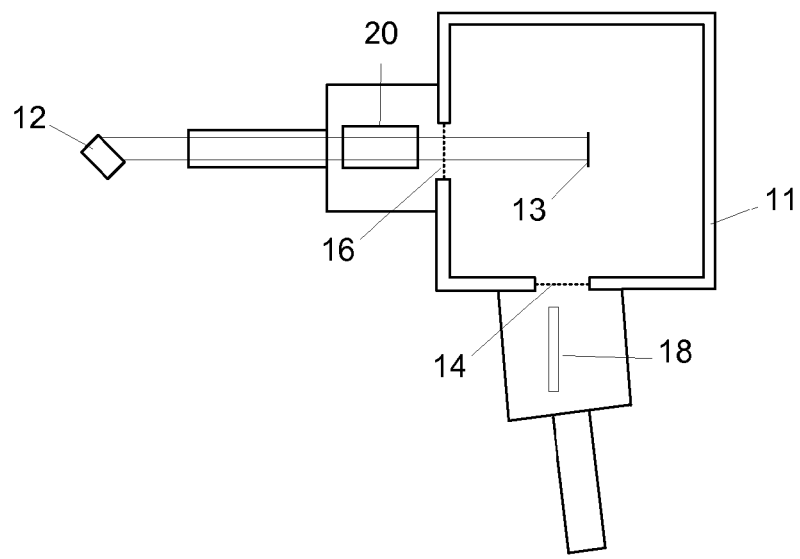
FIG. 2 is a cross-sectional schematic view of the x-ray source of FIG. 1 shown oriented in a second angular position.

In order to allow easy switching between a point focus and a line focus, the housing 10 and optics assemblies 18, 20 are mounted onto a rotary stage. This stage allows the x-ray source to be rotated, along with the optics, relative to the sample position. FIG. 2 shows the x-ray source rotated 90° relative to the orientation of FIG. 1. In the orientation of FIG. 2, the point focus port 14 is inactive, and the line focus port 16 is aligned to provide x-ray energy to the sample 12. The line focus optic 20 receives the line-shaped x-ray beam from the anode 13, conditions it as desired for the application, and directs it to the sample.

Figure 3:
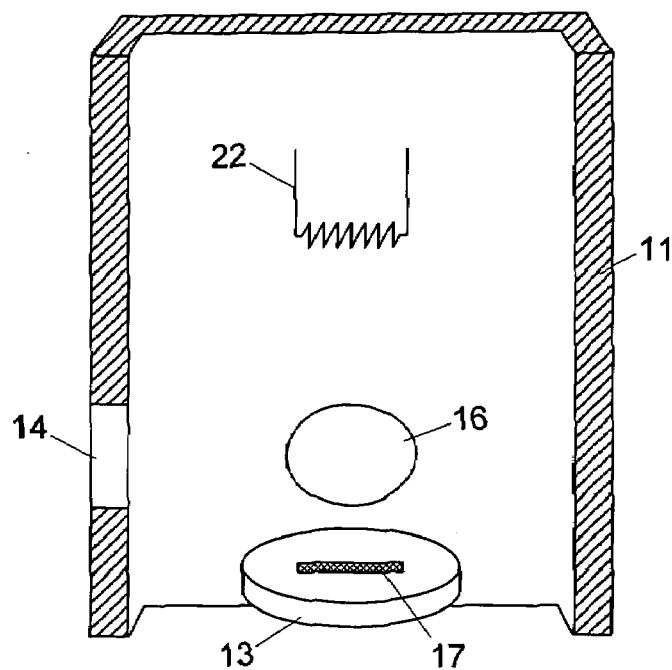
FIG. 3 is a partial cross section schematic view of the interior of an x-ray source housing according to the invention.

Shown in FIG. 3 is a portion of the x-ray source assembly according to the present invention, in which the housing 11 of the source is shown in partial cross section. Within the housing is a cathode 22 that serves as a source of electrons for the anode 13. The active part (or "hot area") 17 of the anode is a linear strip, which provides the desired x-ray beam shapes. As shown, point focus port 14 is positioned at 90° relative to the line focus port 16. Thus, as indicated by the shape of the hot area of the anode 13, the x-rays exiting the point focus port 14, when that port is active, will be in the shape of a spot. When the line focus port 16 is active, the x-rays exiting through that port will be in the shape of a line.

Figure 4:
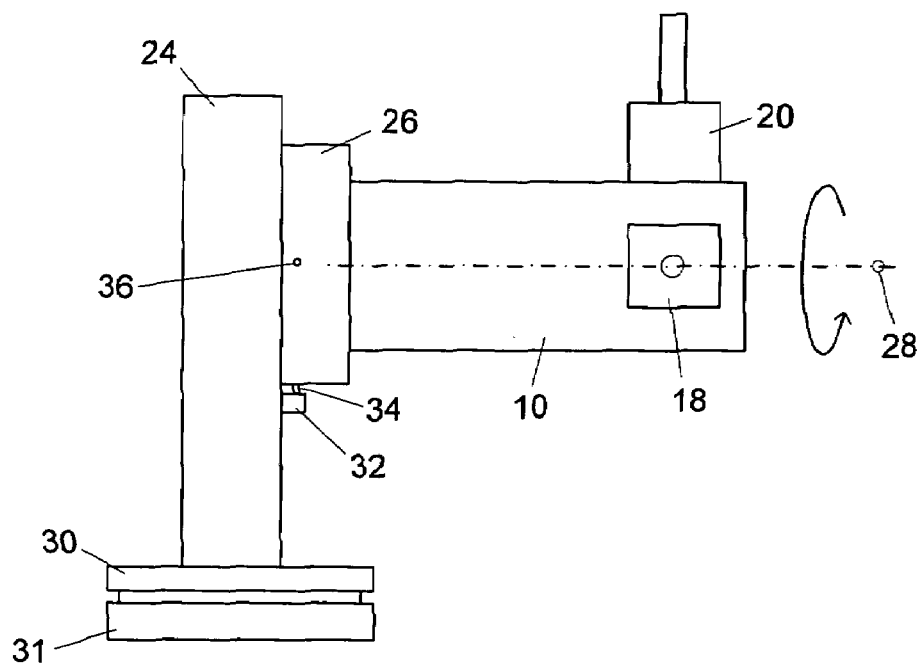
FIG. 4 is a schematic side view of an x-ray source system according to the invention.

A schematic view of the x-ray source 10 as it may be mounted for operation is shown in FIG. 4. The x-ray source is mounted to rotation stage 24, which has a mounting support 26 that may be rotated relative to the remainder of the rotation stage 24. The rotation of support 26 about rotation axis 28 allows the user to position the desired one of the point focus optic 18 or the line focus optic 20 in the active position. In the arrangement shown, the rotation stage 24 is mounted on a movable table 30, which may be used to move the rotation stage in different perpendicular directions relative to the base 31 of the table. In one embodiment, the table is a two-axis movable table that is movable in the vertical direction and one horizontal direction relative to the surface of the base 31. This allows vertical and horizontal positioning of the x-ray source relative to the sample. Those skilled in the art will recognize that other movable mechanisms may also be used with the invention.

The rotation stage 24 may be manually driven or may be motorized to allow a user to easily and rapidly rotate the x-ray source 10 by 90° to align either the point focus optical train or the line focus optical train with the sample. Likewise, the two axis movable table 30 can be driven manually or by motors to move the x-ray beam to the rotation center of the instrument. This may be used, for example, to correct for the different beam deflection in the two cases. If appropriate care is taken with the design of the optics and the rotary stage, the tube may be rotated many times to switch between the two configurations without needing to realign the optics.

A lockout mechanism may also be used for ensuring that only the desired port is active when the x-ray source is in a given rotational position. This may be accomplished in any one of a number of different ways, including the use of mechanical, electrical or software features. In the arrangement shown in FIG. 4, switching contact is made between a stationary element 32 connected to the stationary portion of the rotation stage 24, and a rotatable element 34 connected to the mounting support 26 of the rotation stage. In the position shown, contact between the two switch elements enables the opening of a shutter that normally blocks the point focus port 18 of the x-ray source housing. Another rotating switch element 36 is located at a position 90° away from the switch element 34 along the outer surface of the mounting support 26. Thus, when the mounting support is rotated to move the line focus port into position for use with the sample, the switch element 36 is moved into contact with the stationary element 32, thereby enabling the opening of a shutter of the line focus port. Meanwhile, this rotates the switch element 34 out of contact with the stationary element 32, thereby disabling the shuttering of the point focus port.

Figure 5:
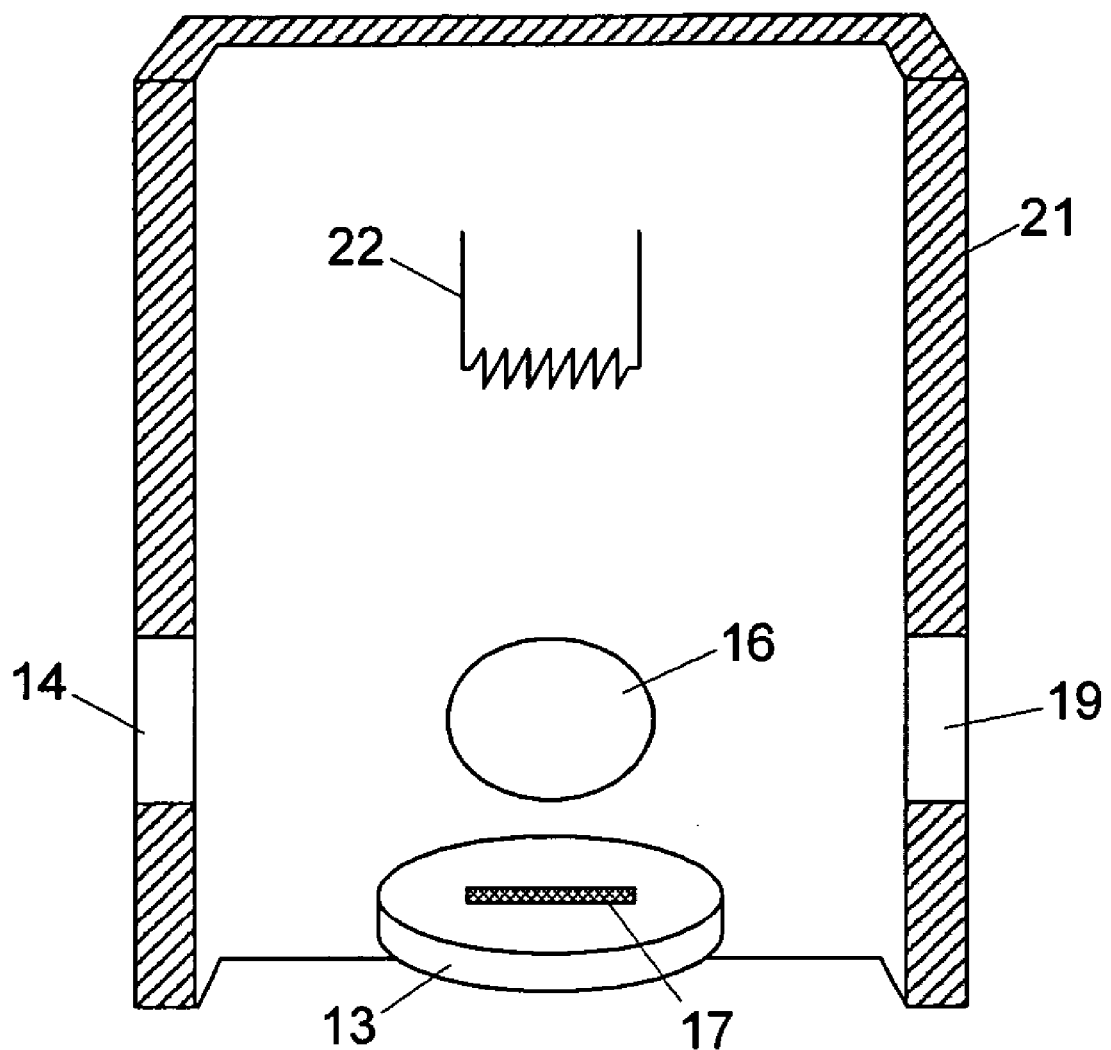
FIG. 5 is a partial cross section schematic view of the interior of an x-ray source housing according to the invention, where the housing has a minimum of three output ports.

In another embodiment of the invention, the x-ray source may have three or four positions, rather than just two. FIG. 5 is a view similar to that of FIG. 4, but shows an x-ray source with a housing 21 having at least three ports (the fourth side of the housing is not depicted in the cross-section shown. Ports 14 and 16 are still present in this housing, as is an additional port 19. Port 19, like port 14, is oriented so that it would received a spot-shaped x-ray beam which may be used with a point source optic attached to the housing 21 adjacent to the port 19. The housing may have a fourth port as well, which would be on the side of the housing 21 opposite port 16 and, like port 16, would receive an x-ray beam having a line shape. An additional optic could therefore be attached to the housing 21 adjacent to this fourth port.

Having four ports would allow the use of all of the port positions of a standard sealed x-ray tube, which produces a linear beam in two opposite directions, and a spot beam in two opposite directions. For example, in a four-position configuration there would be two point focus positions (which could have different focal length optics, for example) and similarly two line focus positions. For a system that used three of the four directions, a housing would have three ports with either two line focus outputs and one point focus output, or two point focus outputs and one line focus output. In a system using ports for all four directions, two point focus outputs and two line focus outputs would be available. For any of these embodiments, the shuttering controls of the various ports of the x-ray source would be arranged to allow only the properly positioned port to be shuttered. A lockout mechanism, such as the one shown in FIG. 4, could be used to ensure that only the desired port was active. A switch element, such as elements 34 and 36, would be positioned for each of the four rotational positions of the x-ray source.

In yet another embodiment of the invention, the x-ray source could be configured to provide different x-ray wavelength outputs. The different wavelengths could be two wavelengths within the output range of a single anode material, or an anode with different materials could be used to generate different wavelengths. An anode having a single target material will typically have a wavelength output spectrum with more than one prominent wavelength (often referred to, respectively, as the "$K_\alpha$" and the "$K_\beta$" radiation). In such a case, one of the optics of the x-ray source could be tuned to the $K_\alpha$ radiation while the other optic was tuned to $K_\beta$ radiation. Thus, by rotating the tube between two positions, the wavelength of the experiment could be easily changed. Depending on the location of these optics, different beam characteristics could be achieved. If the two optics were positioned at 90° relative to each other, a line focus output would be produced at one of the wavelengths, while a point focus output was produced at the other. If the two optics were positioned at 180° relative to each other, two line focus outputs at different wavelengths or two point focuses at different wavelengths could be made available. Those skilled in the art will quickly recognize that all four output directions could be used with optics tuned so that both a line focus output and a point focus output at each of the wavelengths could be made available.

In an x-ray source using a composite anode (say, for example, copper and chromium), a similar result could be achieved. The composite anode would radiate at both the copper wavelength (e.g., copper $K_\alpha$) and at the chromium wavelength (e.g., chromium $K_\alpha$). If two optics were used, the optics could be positioned at 90° to provide a line focus at one wavelength and a point focus at the other. At 180° relative to each other, two line focuses or two point focuses at the different wavelengths would result. Again, the use of all four ports would allow a user to have both line focus and point focus for each of the wavelengths. The rotation stage would allow each of these different x-ray outputs to be selected with ease. Those skilled in the art will also recognize that the composite anode could either have two different areas of different material, in which case the focusing would have to be different for each, or the two materials could be mixed together, and the resulting alloy used with the same focusing for each wavelength. Wavelength selection in any of the multiple wavelength embodiments may be achieved using monochromators or filters.

While the invention has been shown and described with reference to preferred embodiments thereof, it will be recognized by those skilled in the art that various changes in form and detail may be made herein without departing from the spirit and scope of the invention as defined by the appended claims.

What is claimed is:

1. An x-ray source comprising a cathode:
   an anode with an active area from which x-rays are emitted;
   a housing within which the anode is located, the housing having a plurality of output ports through which x-rays can exit, the ports being located along an outer perimeter of the housing at different angular positions relative to the anode; and
   a plurality of x-ray optics, each x-ray optic being connected to an outside of the housing adjacent to one of the output ports so as to condition x-rays exiting that port;
   a rotatable support to which the housing is mounted that allows rotation of the housing and rotation of the connected x-ray optics with the housing to a plurality of different angular orientations, each of which results in a different one of the ports facing a first predetermined direction.

2. An x-ray source according to claim 1 wherein the active area of the anode is oblong in shape.

3. An x-ray source according to claim 1 wherein the anode produces a line focus beam and a point focus beam at an angle of approximately 90° relative to each other.

4. An x-ray source according to claim 1 wherein a first port and a second port of the housing are located at angular positions relative to the anode that are at approximately 90° relative to each other.

5. An x-ray source according to claim 1 wherein the housing has at least four ports.

6. An x-ray source according to claim 1 wherein each of the optics performs a wavelength filtering function.

7. An x-ray source according to claim 1 wherein each of the optics is specifically designed to provide conditioning for either a point focus x-ray beam or a line focus x-ray beam.

8. An x-ray source according to claim 1 wherein the anode is a composite of a plurality of materials, each of which produces x-rays with a different wavelength spectrum.

9. An x-ray source according to claim 8 further comprising a plurality of x-ray optics, each of which is connected to the outside of the housing adjacent to a different one of the ports, the optics each being configured to condition x-rays associated with one of said different wavelength spectra.

10. An x-ray source according to claim 1 wherein the rotatable support is motorized.

11. An x-ray source according to claim 1 further comprising a lockout mechanism that prevents x-rays from exiting any of the ports except for a port that is facing the first direction.

12. An x-ray source according to claim 1 wherein the anode produces an x-ray wavelength spectrum with a plurality of prominent wavelengths, and wherein the x-ray source further comprises a plurality of x-ray optics, each of which is connected to the outside of the housing adjacent to a different one of the ports, and each of which is configured to condition x-rays associated with only one portion of said wavelength spectrum.

13. An x-ray source according to claim 1 further comprising a movable surface upon which the rotatable support is located.

14. An x-ray source according to claim 13 wherein the movable surface is movable in two perpendicular directions.

15. An x-ray system for illuminating a sample material with x-ray energy, the system comprising a cathode:
- an x-ray anode with an oblong active area from which x-rays are emitted, the x-rays forming a beam with a spot-shaped cross section in a first direction S away from the anode, while forming a beam with a line-shaped cross section in a second direction away from the anode that is approximately 90° from the first direction;
- a housing within which the anode is located, the housing having a plurality of output ports through which x-rays can exit, including x-rays traveling in the first direction and the second direction, the ports being located along an outer perimeter of the housing at different angular positions relative to the anode;
- a plurality of x-ray optics, each connected to an outer surface of the housing, and each being adjacent to a different one of the housing ports so as to condition x-ray energy exiting the housing through that port; and
- a rotatable support to which the housing and the x-ray optics are mounted that allows rotation of the housing together with the x-ray optics to a plurality of different angular orientations, each of which results in a different one of the ports facing the sample to allow x-ray energy exiting that port and passing through its associated optic to be directed to the sample so that the sample can be illuminated with conditioned x-ray energy without realigning the x-ray optics.

16. An x-ray system for illuminating a sample material with x-ray energy, the system comprising a cathode:
- an anode with an active area from which x-rays are emitted in a plurality of angular directions, the x-rays in one of said directions having a substantially line-shaped cross section, while the x-rays in another of said directions having a substantially spot-shaped cross section;
- a housing within which the anode is located, the housing having a plurality of output ports through which x-rays can exit, the ports being located on an outer perimeter of the housing aligned with said different angular directions along which x-rays are emitted from the anode;
- a line focus x-ray optic connected to an outer surface of the housing adjacent to one of said ports that is aligned with x-ray energy from the anode that has a line-shaped cross section;
- a point focus x-ray optic connected to an outer surface of the housing adjacent to one of said ports that is aligned with x-ray energy from the anode that has a spot-shaped cross section; and
- a rotatable support to which the housing, the line focus x-ray optic and the point focus x-ray optic are mounted that allows rotation of the housing together with the line focus x-ray optic and the point focus x-ray optic to a plurality of different angular orientations, a first of which results in the line focus optic being oriented such that x-ray energy passing through it reaches the sample, and a second of which results in the point focus optic being oriented such that x-ray energy passing through it reaches the sample so that the sample can be illuminated with both line-focused and point focused x-ray energy without realigning the line focus and the point focus x-ray optics.

17. An x-ray system according to claim 16 further comprising additional ports and additional optics, each additional optic being connected to an outer surface of the housing adjacent to one of the additional ports.

18. An x-ray system according to claim 16 wherein each of the optics performs a wavelength filtering function.

19. An x-ray system according to claim 16 wherein the anode is a composite of a plurality of materials, each of which produces x-rays with a different wavelength spectrum.

20. An x-ray system according to claim 19 wherein the line focus optic and the point focus optic are each configured to condition x-rays associated with a different one of said different wavelength spectra.

21. An x-ray system according to claim 16 wherein the anode produces an x-ray wavelength spectrum with a plurality of prominent wavelengths, and wherein each of the line focus optic and the point focus optic are configured to condition x-rays associated with only one portion of said wavelength spectrum.

22. An x-ray system according to claim 16 further comprising a movable surface upon which the rotatable support is located.

23. An x-ray system according to claim 22 wherein the movable surface is movable in two perpendicular directions.

* * * * *

UNITED STATES PATENT AND TRADEMARK OFFICE
CERTIFICATE OF CORRECTION

PATENT NO. : 7,248,672 B2 Page 1 of 1
APPLICATION NO. : 11/111497
DATED : July 24, 2007
INVENTOR(S) : Roger D. Durst and Bob Baoping He It is certified that error appears in the above-identified patent and that said Letters Patent is hereby corrected as shown below:

Column 7,
Line 10, please replace "direction S away" with --direction away--.

Signed and Sealed this

Sixteenth Day of December, 2008

JON W. DUDAS
*Director of the United States Patent and Trademark Office*